Dec. 8, 1959 R. G. JELLY Plant Pat. 1,887
ROSE PLANT
Filed March 26, 1959
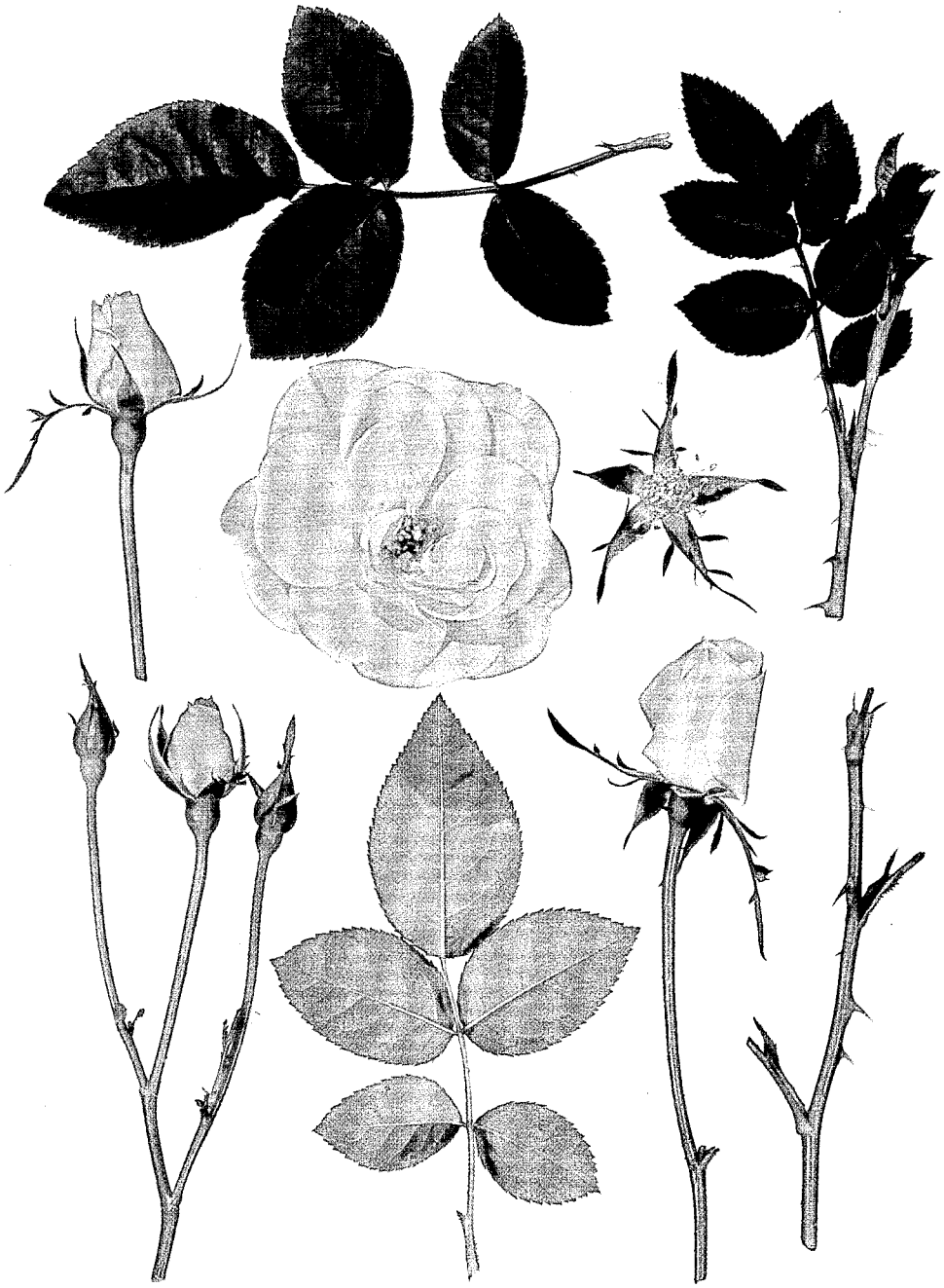
INVENTOR
R. G. Jelly
BY Robb & Robb
ATTORNEYS United States Patent Office Plant Pat. 1,887
Patented Dec. 8, 1959

1,887

ROSE PLANT

Robert G. Jelly, Richmond, Ind., assignor to E. G. Hill Co., Inc., Richmond, Ind., a corporation of Indiana Application March 26, 1959, Serial No. 802,274

1 Claim. (Cl. 47—61)

The present invention relates to a new and distinct variety of rose plant of the polyantha class, which was originated by me by crossing the variety "Garnette" (unpatented) with an unnamed and unpatented pink hybrid tea seedling identified in my breeding records as No. 11–50.

The primary objective of this breeding was to produce a new rose variety in which there is combined the good growth, vigor and flower keeping qualities of the parent variety "Garnette," and the extremely attractive and good keeping qualities of the flowers of the unnamed pink seedling parent. These features were fully attained, along with other desirable improvements, as evidenced by the following unique combination of characteristics which are outstanding in the new variety and which distinguish it from its parents as well as from all other varieties of which I am aware:

(1) Good habits of growth comparable to those of "Garnette";

(2) Excellent flower productivity;

(3) Good flower stem length suitable for commercial cut flowers;

(4) Good flower size;

(5) Good flower keeping qualities; and (6) An attractive and distinctive pink, with yellow base, general color tonality of the blooms.

In comparison with its seed parent, "Garnette," the flowers of my new variety are slightly larger and are borne on longer stems, while the good keeping quality of the blooms of this parent are retained, and the flower color of the new variety is pink, as distinguished from the red flower color of this parent.

As compared with its unnamed seedling pollen parent (which was a rose of the large hybrid tea class), the new variety is of the floribunda class and retains much of the good growth habits and flower color of the parent variety.

Asexual reproduction of the new variety by budding, as performed in Texas, and by grafting, as performed by me at Richmond, Indiana, shows that the foregoing characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character.

The following is a detailed description of the new variety, with color terminology in accordance with Robert S. Wilson's Horticultural Colour Chart (hereinafter abbreviated as "Wilson") and Ridgway's Color Standards and Nomenclature (hereinafter abbreviated as "Ridgway"), as indicated:

Type: Seedling; greenhouse; for cut flower production.
Class: Polyantha.
Breeding: Seedling.

*Seed parent.*—"Garnette."

*Pollen parent.*—An unnamed pink hybrid tea seedling.

Propagation: Holds its distinguishing characteristics through succeeding propagations by budding and grafting.

*Flower*

Locality where grown and observed: Richmond, Indiana.
Flowers borne: From 1 to 3 to stem; on moderately strong stems of from short to medium length.
Quantity of bloom: Abundant and free, in greenhouse.
Continuity: Continuous, in greenhouse.
Fragrance: Slight, in greenhouse. Nature—sweetbriar.

Bud:

*Peduncle.*—Medium length; from small to medium diameter; erect. Bark—slightly rough; color—Lettuce Green, Plate V (Ridgway). Thorns—none. Prickles—numerous; color—Pale Yellow Green, Plate VI (Ridgway). Hairs—none.

*Before calyx breaks.*—Size—small. Form—short pointed; with a conspicuous neck; with foliaceous appendages on the surface of the bud; with much-cut, bristle-like foliaceous parts extending beyond the tip of the bud equal to ¾ or more of its length. Color—Spinach Green, Plate V (Ridgway).

*As calyx breaks.*—Color—Carmine Rose, Plate 621 (Wilson).

*As first petal opens.*—Size—small. Form—short pointed. Color: outside—Dawn Pink, Plate 523 (Wilson), with base Aureolin, Plate 3/2 (Wilson); inside—Carmine Rose, Plate 621 (Wilson), with base Aureolin, Plate 3/2 (Wilson).

*Opening.*—Opens up well in greenhouse; is affected by hot weather by very slight fading of bloom color, and slightly smaller bud.

Bloom:

*Size (when fully open).*—From 2½ to 3 inches.

*Petalage.*—Double; from 30 to 38 petals; arranged regularly.

*Form.*—Very high-centered at first, but becoming flat; petals being at first very tightly rolled inward, but becoming later at maturity very loosely rolled.

Petals:

*Texture.*—Moderately thin and soft. Inside—satiny. Outside—dull.

*Shape.*—Outer—obovate, with apex mucronate, and usually with 1 notch, but sometimes none. Intermediate—obovate, with apex flat. Inner—oval, with apex flat.

This description of a newly opened flower was made from a rose grown in a greenhouse in the month of September at Richmond, Indiana:

*Color.*—Outer petal: outside surface—Neyron Rose, Plate 623/3 (Wilson), with base Aureolin, Plate 3/2 (Wilson); inside surface—Camellia Rose, Plate 622/2 (Wilson), with base Canary Yellow, Plate 2/2 (Wilson). Intermediate petal: outside surface—Carmine Rose, Plate 621/1 (Wilson), with base Aureolin, Plate 3/2 (Wilson); inside surface—Camellia Rose, Plate 622/1 (Wilson), with base Aureolin, Plate 3/1 (Wilson). Inner petal: outside surface—Carmine Rose, Plate 621/1 (Wilson), with base Aureolin, Plate 3/2 (Wilson); inside surface—Carmine Rose, Plate 621/1 (Wilson), with base Aureolin, Plate 3/1 (Wilson).

This description was made from a rose that was open for 3 days in a greenhouse in the month of September, at Richmond, Indiana:

*Color.*—Outer petal: outside surface—Carmine

Rose, Plate 621/3 (Wilson), with base Chartreuse Green, Plate 663/3 (Wilson); inside surface—Camellia Rose, Plate 622/3 (Wilson), with base Chartreuse Green, Plate 663/3 (Wilson). Intermediate petal: outside surface—Neyron Rose, Plate 623/2 (Wilson), with base Aureolin, Plate 3/2 (Wilson); inside surface—Neyron Rose, Plate 623/2 (Wilson), with base Aureolin, Plate 3/2 (Wilson). Inner petal: outside surface—Neyron Rose, Plate 623/2 (Wilson), with base Aureolin, Plate 3/2 (Wilson); inside surface—Neyron Rose, Plate 623/2 (Wilson), with base Aureolin, Plate 3/2 (Wilson).

*General color effect.*—Newly opened flower—Neyron Rose, Plate 623 (Wilson). 3-days open—Neyron Rose, Plate 623/2 (Wilson).

*Behavior.*—Persist in greenhouse; affected by hot weather by slight decrease in bud size and fading of color to Neyron Rose, Plate 623/2 (Wilson) after 6 days on plant.

*Flower longevity.*—Cut roses grown in greenhouse and kept at living-room temperatures—7 days in April.

*Plant*

Foliage:

*Leaves.*—Compound of from 3 to generally 5 leaflets; normal abundance; medium size; moderately thin and slightly glossy.

*Leaflets.*—Shape—from oval to ovoid, with apex cuspidate. Base—obtuse. Margin—from simply to doubly serrate.

*Color.*—Mature: upper surface—Dark Dull Yellow Green, Plate XXXII (Ridgway); under surface—Lavender Green, Plate 000761 (Wilson). Young: upper surface—Dark Vinaceous Brown, Plate XXXIX (Ridgway); under surface—Indian Red, Plate XXVII (Ridgway).

*Rachis (the supporting stem of the compound leaf.*—Light. Upper side—grooved; prickly. Under side—prickly, and with a few tiny thorns.

*Stipules.*—Moderately short; narrow; with short points turning out at an angle of 45°.

Growth (in greenhouse):

*Habit.*—Bush; upright; much-branched.

*Growth.*—Free; vigorous.

*Canes.*—Small.

*Main stems.*—Color—Hellebore Green, Plate XVII (Ridgway). Thorns—several; medium length; hooked slightly downward; with long, narrow base; color—Tawny Olive, Plate XXIX (Ridgway). Prickles—none. Hairs—none.

*Branches.*—Color—Spinach Green, Plate 0960/1 (Wilson). Thorns—several; medium length; hooked downward; with long, narrow base; color—Kildare Green, Plate XXXI (Ridgway). Prickles—none. Hairs—none.

*New shoots.*—Color—Spinach Green, Plate 0960/3 (Ridgway). Thorns—several; long; hooked downward; with long, narrow base; color—Dull Green-Yellow, Plate XVII (Ridgway). Prickles—some shoots have several; other shoots have none; color—Pale Dull Green-Yellow, Plate XVII (Ridgway). Hairs—none.

*Reproductive organs*

Stamens: Medium number; arranged regularly about pistils; tucked in calyx.

Filaments: Short; most with anthers. Color—Chartreuse Yellow, Plate XXXI (Ridgway).

Anthers: Small; open at various times. Color—Ochraceous-Tawny, Plate XV (Ridgway).

Pollen: Sparse. Color—Raw Sienna, Plate III (Ridgway).

Pistils: Few.

Styles: Even; short; moderately thin; loosely bunched; columnar. Color—Pale Green-Yellow, Plate V (Ridgway).

Stigma: Color—Buff Yellow, Plate IV (Ridgway).

Ovaries: All enclosed in calyx.

Hips (immature): Medium length; oblong; with a conspicuous neck; pear-shaped; smooth; walls thin. Color—Biscay Green, Plate VII (Ridgway).

Sepals: Permanent; moderately short; spear-shaped; recurved.

Seeds: Few; small.

I claim:

A new and distinct variety of rose plant of the polyantha class, substantially as herein shown and described, characterized particularly as to novelty by the unique combination of good habits of growth, excellent flower productivity, good flower stem length suitable for commercial cut flowers, good flower size and keeping qualities, and an attractive pink, with yellow base, general color tonality of the blooms.

No references cited.